(12) United States Patent
McCarty

(10) Patent No.: US 11,077,086 B2
(45) Date of Patent: Aug. 3, 2021

(54) SOLID DOSAGE FORM COMPOSITION FOR BUCCAL OR SUBLINGUAL ADMINISTRATION OF CANNABINOIDS

(71) Applicant: PHARMACEUTICAL PRODUCTIONS, INC., Miami Springs, FL (US)

(72) Inventor: John A. McCarty, Miami Springs, FL (US)

(73) Assignee: Pharmaceutical Productions, Inc., Miami Springs, FL (US)

(*) Notice: Subject to any disclaimer, the term of this patent is extended or adjusted under 35 U.S.C. 154(b) by 0 days.

(21) Appl. No.: 14/804,384

(22) Filed: Jul. 21, 2015

(65) Prior Publication Data

US 2016/0015683 A1    Jan. 21, 2016

Related U.S. Application Data

(60) Provisional application No. 61/999,300, filed on Jul. 22, 2014, provisional application No. 61/999,239, filed on Jul. 21, 2014.

(51) Int. Cl.
*A61K 31/352* (2006.01)
*A61J 3/00* (2006.01)
*A61K 9/00* (2006.01)
*A61K 9/20* (2006.01)
*A61K 31/05* (2006.01)

(52) U.S. Cl.
CPC ........... *A61K 31/352* (2013.01); *A61J 3/007* (2013.01); *A61K 9/0056* (2013.01); *A61K 9/2009* (2013.01); *A61K 9/2018* (2013.01); *A61K 9/2054* (2013.01); *A61K 31/05* (2013.01)

(58) Field of Classification Search
CPC combination set(s) only.
See application file for complete search history.

(56) References Cited

U.S. PATENT DOCUMENTS

| | | |
|---|---|---|
| 4,876,276 A | 10/1989 | Mechoulam et al. |
| 5,047,244 A | 9/1991 | Sanvordeker et al. |
| 5,227,537 A | 7/1993 | Stoss et al. |
| 5,434,295 A | 7/1995 | Mechoulam et al. |
| 6,730,330 B2 | 5/2004 | Whittle et al. |
| 6,946,150 B2 | 9/2005 | Whittle |
| 7,025,992 B2 | 4/2006 | Whittle et al. |
| 7,648,696 B2 | 1/2010 | McPhillips et al. |
| 7,709,536 B2 | 5/2010 | Whittle |
| 8,211,946 B2 | 7/2012 | Whittle |
| 8,222,292 B2 | 7/2012 | Goskonda et al. |
| 8,449,908 B2 | 5/2013 | Stinchcomb et al. |
| 8,481,091 B2 | 7/2013 | Ross |
| 8,512,767 B2 | 8/2013 | Ross |
| 8,603,515 B2 | 12/2013 | Whittle |
| 8,642,645 B2 | 2/2014 | Kelly |
| 8,735,374 B2 | 5/2014 | Zerbe et al. |
| 8,790,719 B2 | 7/2014 | Parolaro et al. |
| 2004/0034108 A1* | 2/2004 | Whittle ............... B65D 65/38 514/772 |
| 2004/0192760 A1 | 9/2004 | Whittle et al. |
| 2010/0119601 A1 | 5/2010 | McCarty |
| 2013/0059018 A1 | 3/2013 | Parolaro et al. |

FOREIGN PATENT DOCUMENTS

| | | |
|---|---|---|
| EP | 2298284 A2 | 3/2011 |
| EP | 2609912 A1 | 7/2013 |
| WO | 2003063847 A1 | 8/2003 |
| WO | WO-2005/087199 A2 | 9/2005 |
| WO | 2008144475 A1 | 11/2008 |
| WO | 2011063164 A2 | 5/2011 |

OTHER PUBLICATIONS

Agurell et al. (1986) Pharmacokinetics and Metabolism of Delta 1-Tetrahydrocannabinol and Other Cannabinoids With Emphasis on Man, Pharmacol. Revs. 38(1)21-43.
Carlini et al. (1981) Hypnotic and Antiepileptic Effects of Cannabidiol, J. Clin. Pharmacol. 21:417S-427S.
Colasanti et al. (1984) Ocular Hypotension, Ocular Toxicity, and Neurotoxicity in Response to Marihuana Extract and Cannabidiol, Gen. Pharmac.15(6):479-484.
Colasanti et al. (1984) Intraocular Pressure, Ocular Toxicity and Neurotoxicity After Administration of Cannabinol or Cannabigerol, Exp. Eye Res. 39:251-259.
Consroe et al. (1981) Antiepileptic Potential of Cannabidiol Analogs, J. Clin. Pharmacol. 21:428S-436S.
Karler et al. (1981) The Cannabinoids as Potential Antiepileptics, J. Clin. Pharmacol. 21:437S-448S.
Rachid et al. (2011) Dissolution Testing of Sublingual Tablets: A Novel in Vitro Method, AAPS PharmSciTech 12(2):544-552.
International Search Report and Written Opinion, PCT/US2015/041232, dated Oct. 15, 2015 (12 pages).

* cited by examiner

*Primary Examiner* — Kortney L. Klinkel
*Assistant Examiner* — Tori Strong
(74) *Attorney, Agent, or Firm* — Honigman LLP; Andrew S. Chipouras; Jonathan P. O'Brien

(57) ABSTRACT

The present invention relates to solid dosage forms of cannabinoid pharmaceutical formulations comprising a solvated cannabinoid for buccal or sublingual administration, and methods of making and using the same.

18 Claims, 2 Drawing Sheets

SOLID DOSAGE FORM COMPOSITION FOR BUCCAL OR SUBLINGUAL ADMINISTRATION OF CANNABINOIDS

CROSS-REFERENCE TO RELATED APPLICATIONS

This application claims the benefit of U.S. Provisional Application No. 61/999,239 filed on Jul. 21, 2014 and U.S. Provisional Application No. 61/999,300 filed on Jul. 22, 2014, which are hereby expressly incorporated by reference into the present application.

FIELD OF INVENTION

The present invention relates to the field of cannabinoids and their use as supplements and therapeutics formulations. More specifically this invention relates to sublingual or buccal solid dosage forms of cannabinoids.

BACKGROUND

Cannabinoids are a group of chemicals found in *Cannabis sativa, Cannabis indica*, and related plant species. They are known to activate cannabinoid receptors (CB1 and CB2) in, e.g., mammalian brain cells. These chemicals are also produced endogenously in humans and other animals. Cannabinoids are cyclic molecules exhibiting particular properties such as being lipophilic, have the ability to easily cross the blood-brain barrier, and having low toxicity. As such, cannabinoids have been used to treat medical illnesses such as AIDS and cancer which are often accompanied with a lack of appetite. Moreover, patients receiving cancer chemotherapy often experience nausea and vomiting side effects for which cannabinoids can be helpful (see, e.g., WO 03/063847). Chronic pain (e.g., neuropathic pain), malignant tumors, spasticity (in multiple sclerosis and spinal cord injury), and dystonia are additional therapeutic targets for cannabinoid therapy. In addition, one cannabinoid, cannabidiol, has been studied as an antiepileptic (Carlini et al. (1981) *J. Clin. Pharmacol.* 21:417S-427S; Karler et al. (1981) *J. Clin. Pharmacol.* 21:437S-448S; Consroe et al. (1981) *J. Clin. Pharmacol.* 21:428S-436S), and also has been found to lower intraocular pressure (Colasanti et al. (1984) *Exp. Eye Res.* 39:251-259; Colasanti et al. (1984) *Gen. Pharmacol.* 15:479-484). Cannabinoids have been shown to have an anti-proliferative effect on cancers (see, e.g., US 20130059018 A and WO 2008/144475).

There are currently several methods of cannabinoid delivery. Lung delivery is most commonly achieved by smoking *cannabis*. However, there are health concerns for this mode of administration. *Cannabis* smoke carries even more tars and other particulate matter than tobacco, so it may cause a loss of lung function or cancer. Furthermore, many patients find the act of smoking unappealing, as well as being generally unhealthy. For these reasons, smoking *cannabis* is not acceptable as a medical means of administration.

Attempts have been made to overcome some of the problems associated with smoking both *cannabis* and tobacco by providing various smokeless inhalable aerosol formulations for lung delivery. An inhalable aerosol of delta-9-tetrahydro-cannabinol (THC) was developed as long ago as 1975 as a bronchodilator. These formulations were found to be of varying effectiveness in delivering the active agent to the lungs and compliance was an issue even with proper training on the use of inhalation devices.

Attempts have also been made at administering the cannabinoid delta 9-THC orally in the form of a liquid filled soft gelatin capsule, Miranol®. However, severely nauseated patients are often not able to retain the capsules in their stomachs long enough for the drug to take effect. This problem is compounded by the fact that four to six capsules may be required and this just before taken chemotherapy. It has also been found that cannabinoids have poor oral bioavailability, and thus orally administered THC is erratically and slowly absorbed into the bloodstream, making the dose and timing of action difficult to control. Indeed, the oral bioavailability of Miranol® is very poor, ranging from 5-20% due to cannabinoids being broken down by the liver resulting in high first-pass metabolism. Therefore, the oral administration of cannabinoids requires larger doses for which the absorption is erratic and uncontrolled for both dose and onset of drug action.

In order to overcome the limitations associated with inhaled and oral cannabinoid delivery, other cannabinoid delivery systems have been developed, e.g., aerosol and pump spray delivery systems for the oral mucosa. These systems (e.g. Sativex®) also show a high degree of variability in pharmacokinetic parameters such as dose delivered, time to maximum drug plasma levels and maximum plasma levels.

Attempts have also been made to improve oral delivery of cannabinoids by use of organic acids, essential oils and lecithin and other excipient and through complexation with cyclodextrin. Transdermal preparations have also been attempted.

Thus, the commercially available cannabinoid delivery systems have erratic absorption and poor bioavailability. Therefore, there is real unmet medical need for improved modes of cannabinoid delivery.

A common problem associated with transmucosal administration via the buccal route, is swallowing the dose due to the continuous secretion of saliva in the oral cavity. This contributes to observed pharmacokinetics variability of oral cannabinoid sprays and aerosols. For optimal drug delivery the buccal and sublingual dosage forms must remain in contact with oral mucosa for a time sufficient to allow for the absorption of a pharmaceutically active agent. More specifically, the dosage form must not be washed away by saliva into the gastrointestinal tract. However, the rate of disintegration or dissolution of the dosage form must not be so slow as to cause discomfort or inconvenience for the patient. Additionally, suitable buccal and sublingual dosage forms should be small in size and designed so that the shape avoids discomfort to the patient during use. Most importantly the formulation must be designed so that the cannabinoid is in a solution which optimizes its transmucosal permeation.

The sublingual/buccal composition described herein is a convenient, safe, fast acting, solid oral dosage form which provides accurate and timely cannabinoid delivery with increased oral bioavailability as it avoids swallowing the dosage and subsequent high first-pass metabolism associated with gastrointestinal absorption of cannabinoids.

SUMMARY OF THE INVENTION

It has been discovered that a solid dosage form for the sublingual/buccal administration of solvated cannabinoids is able to achieve satisfactory or therapeutic plasma levels in a mammalian subject, with fast onset of drug action and improved oral bioavailability compared to the currently marketed cannabinoid products.

This discovery has been exploited to develop the present invention, which, in one aspect, provides a composition comprising a pharmaceutical composition in a solid dosage form for sublingual or buccal administration, comprising: a cannabinoid; a pharmaceutically-acceptable solvent into which the cannabinoid is solvated; and a pharmaceutically-acceptable adsorbent onto which the solvated cannabinoid is adsorbed.

In some embodiments, the solvent comprises a polyethylene glycols (PEG) propylene glycol, a substituted polyethylene glycol, propylene carbonate, ethanol, ethyl acetate, isopropyl alcohol, triacetin, triethyl citrate, tributyl citrate, substituted polyethylene glycols, bisabolol, glycerin, mineral oil, ethyl oleate, oleic acid, fatty acid esters, lactic acid, dipropylene glycol, hexylene glycol, propylene carbonate, benzyl benzoate, benzyl alcohol, perillyl alcohol, dibutyl sebacate, phenyethyl alcohol, n-methyl pyrrolidone, dimethyl sulfoxide, 2-pyrrolidone, squalane, an animal oil, a vegetable oil, dimethyl isosorbide, hydrogenated vegetable oils, isopropyl myristate, limonene, isopropyl palmitate, glycofurol, a terpene, an essential oil, an alcohol, a diol, a polyol, a silicone fluid, or combinations thereof. In certain embodiments, the solvent comprises polyethylene glycol, ethanol, substituted polyethylene glycols, propylene glycol, propylene carbonate, or a mixture thereof. In other embodiments, the solvent comprises ethanol.

In some embodiments, the adsorbent comprises silica, microcrystalline cellulose, cellulose, silicified microcrystalline cellulose, clay, talc, starch, pregelatinized starch, calcium carbonate, dicalcium phosphate, magnesium carbonate, and mixtures thereof. In particular embodiments, the adsorbent comprises silica. In certain embodiments, the adsorbent comprises silicon dioxide, amorphous silica, hydrated silicon dioxide, fumed silica, colloidal silicon dioxide, magnesium aluminum silicate, magnesium silicate, calcium silicate, or a mixture thereof. In specific embodiments, the adsorbent comprises ZEOPHARM 5170, AEROSIL 200, CABOSIL MP5, AEROPERL 300, SYLOID 244FP, SYLOID 63FP, SYLOID 72 FP, SIPERNAT 160PQ, SIPERNAT 50, SIPERNAT 50S, SYLOID 3050, SYLOID 3150, SIPERNAT 500LS, SIPERNAT 2200, SIDENT 8, SIDENT 9, SIDENT 10, SIDENT 22S. In some embodiments, the cannabinoid comprises cannabidiol (CDB), 11-hydroxy-delta-8-tetrahydro-cannabinol, and 11-hydroxy-delta-9-tetrahydrocannabinol (THC). Other cannabinoids include dimethyl heptylpentyl cannabidiol (DMHP-CBD), 6,12-dihydro-6-hydroxy-cannabidiol (see, e.g., U.S. Pat. No. 5,227,537); (3S,4R)-7-hydroxy-Δ6-tetrahydrocannabinol homologs and derivatives (described in U.S. Pat. No. 4,876,276); (+)-4-[4-DMH-2,6-diacetoxy-phenyl]-2-carboxy-6,6-dimethylbicyclo[3.1.1]hept-2-en, and other 4-phenylpinene derivatives (see, e.g., U.S. Pat. No. 5,434,295), and cannabidiol (−)(CBD) analogs such as (−)CBD-monomethylether, (−)CBD dimethyl ether; (−)CBD diacetate; (−)3'-acetyl-CBD monoacetate; and ±AF11 (see, e.g., Consroe et al. (1981) *J. Clin. Pharmacol.* 21:428S-436S), cannaichromene (CBC), cannabichromenic acid (CBCV), cannabidiolic acid (CBDA), cannabidivarin (CBDV), cannabigerol (CBG), cannabigerol variant (CBGV), cannabicyclol (CBL), cannabicyclol (CBN), tetrahydrocannabivarin (THCV), tetrahydrocannabivarinic acid (THCVA), cannabitriol (CBO), cannabinol propyl variant (CBNV), and tetrahydrocannabinolic acid (THCA). In certain embodiments, the cannabinoid comprises delta-9-tetrahydrocannabinol (THC). In some embodiments, the THC is present at from about 0.5 mg to about 50 mg or from about 10 mg to about 30 mg. In other embodiments, the cannabinoid is cannabidiol (CBD). In some embodiments, the CBD is present at from about 0.5 mg to about 50 mg or from about 10 mg to about 30 mg.

In some embodiments, the concentration of the solvent is from about 0.5% to about 95.0%, from about 1% to about 80%, from about 5% to about 7%, or from about 15% to about 35% weight/weight solvent to cannabinoids. In certain embodiments, the weight/weight ratio of silica:cannabinoid solution is from about 1:0.5 to about 1:5.

The compositions according to the disclosure may further comprise a water-soluble diluent, a disintegrant, a lubricant, or mixtures thereof. In some embodiments, the diluent comprises mannitol. In certain embodiments, the disintegrant comprises low-substituted hydroxypropyl cellulose. In particular embodiments, the lubricant comprises sodium stearyl fumarate.

In some embodiments, the composition is in the form of a tablet or film.

Also provided in another aspect is a method for preparing a pharmaceutical composition comprising a solvated cannabinoid in a solid dosage form for sublingual or buccal administration having increased oral bioavailability and shortened onset of action of the cannabinoid. The method comprises: solvating the cannabinoid in a pharmaceutically acceptable solvent to form a solvated cannabinoid; mixing the solvated cannabinoid with an adsorbent, onto which the solvated cannabinoid is adsorbed; and processing the solvated cannabinoid/adsorbent into a solid dosage form.

In some embodiments. the cannabinoid is THC or CBD. In certain embodiments, the adsorbent comprises silica. In particular embodiments, the solvent comprises ethanol.

In particular embodiments, the method further comprising adding an excipient to the solvated cannabinoid/adsorbent. In specific embodiments, the excipient added is a lubricant, a water-soluble diluent, a disintegrant, or a mixture thereof. In some embodiments, the lubricant comprises sodium stearyl fumarate. In certain embodiments, the diluent comprises mannitol. In particular embodiments, the disintegrant comprises low-substituted hydroxypropyl cellulose.

In some embodiments, the method further comprises processing the solvated cannabinoid/adsorbent composition into a tablet.

In another aspect, the disclosure provides a pill pack comprising the cannabinoid composition of claim 1 encased within a packaging enclosure.

In yet another aspect, the disclosure provides a method of treating a disease in a subject in need thereof, for which a cannabinoid is an effective therapeutic, comprising: buccally or sublingually administering the cannabinoid composition of claim 1 to the subject by placing the composition in an oral cavity of the subject, whereby a therapeutically effective amount of the cannabinoid is administered.

BRIEF DESCRIPTION OF THE DRAWINGS

The foregoing and other objects of the present disclosure, the various features thereof, as well as the invention itself may be more fully understood from the following description, when read together with the accompanying drawings in which.

DESCRIPTION

Figure 1:
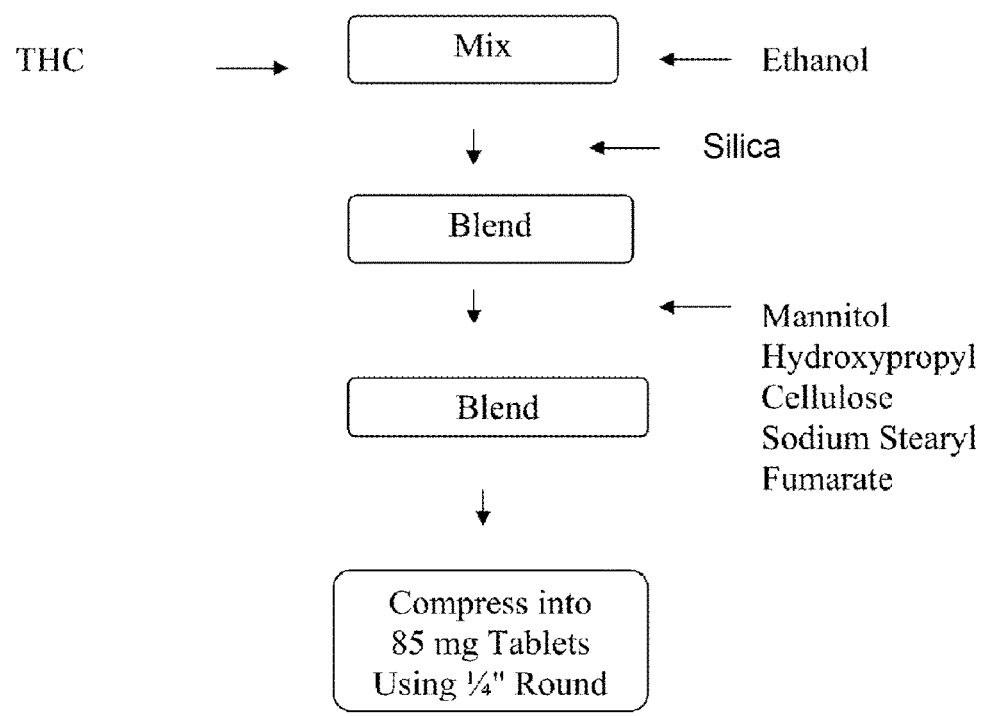
FIG. 1 is a flow chart showing steps comprising the manufacture of an exemplary composition according to the disclosure in the form of a sublingual tablet containing THC as described in Example 1.

The issued U.S. patents, allowed applications, published foreign applications, and references that are cited herein are hereby incorporated by reference in their entirety to the same extent as if each was specifically and individually indicated to be incorporated by reference. Patent and scientific literature referred to herein establishes knowledge that is available to those of skill in the art.

Unless otherwise defined, all technical and scientific terms used herein have the same meaning as commonly understood by one of ordinary skill in the art to which this disclosure belongs.

The present disclosure provides a cannabinoid composition comprising a solid dosage form for sublingual and buccal administration. The composition comprises a cannabinoid, a solvent or mixture of solvents into which the cannabinoid is solvated, and an adsorbent onto which the solvated cannabinoid is adsorbed. It has been discovered that the combination of the solvated cannabinoid mixed with the adsorbent which when formulated into a solid dosage form for sublingual/buccal administration unexpectedly improves oral bioavailability with fast onset of cannabinoid action compared to other prior art forms for oral delivery of cannabinoids. This composition prepared in accordance with the method of the disclosure thereby unexpectedly provides an unmet medical need for a convenient, safe, fast acting, solid oral dosage form which provides accurate and timely cannabinoid delivery with increased oral bioavailability as it avoids swallowing the dosage and subsequent high first-pass metabolism associated with gastrointestinal absorption of cannabinoids.

For purposes of the present invention, the term "cannabinoid" includes any member of naturally occurring and synthetic cannabinoids and related compounds, and extracts from any *Cannabis* species and varieties. The cannabinoids may be natural, semi-synthetic, or synthetic. They may be included in its free form, or in the form of a salt; an acid addition salt of an ester; an amide; an enantiomer; an isomer; a tautomer; a prodrug; different isomeric forms (for example, enantiomers and diastereoisomers), both in pure form and in admixture, including racemic mixtures. Cannabinoids include compounds (such as THC) that have high affinity for the cannabinoid receptor (for example Ki<250 nM), and compounds that do not have significant affinity for the cannabinoid receptor (such as cannabidiol (CBD)). Cannabinoids also include compounds that have a characteristic dibenzopyran ring structure (of the type seen in THC) and cannabinoids which do not possess a pyran ring (such as cannabidiol). The term "cannabinoid" is also meant to encompass derivatives that are produced from another compound of similar structure by the replacement of, e.g., substitution of one atom, molecule or group by another, e.g., cannabidiol (CDB), 11-hydroxy-delta-8-tetrahydro-cannabinol, and 11-hydroxy-delta-9-tetrahydrocannabinol (THC). Other cannabinoids include dimethyl heptylpentyl cannabidiol (DMHP-CBD), 6,12-dihydro-6-hydroxy-cannabidiol (see, e.g., U.S. Pat. No. 5,227,537); (3S,4R)-7-hydroxy-Δ6-tetrahydrocannabinol homologs and derivatives (described in U.S. Pat. No. 4,876,276); (+)-4-[4-DMH-2,6-diacetoxyphenyl]-2-carboxy-6,6-dimethylbicyclo[3.1.1]hept-2-en, and other 4-phenylpinene derivatives (see, e.g., U.S. Pat. No. 5,434,295), and cannabidiol (−)(CBD) analogs such as (−)CBD-monomethylether, (−)CBD dimethyl ether; (−)CBD diacetate; (−)3'-acetyl-CBD monoacetate; and ±AF11 (see, e.g., Consroe et al. (1981) *J. Clin. Pharmacol.* 21:428S-436S), cannaichromene (CBC), cannabichromenic acid (CBCV), cannabidiolic acid (CBDA), cannabidivarin (CBDV), cannabigerol (CBG), cannabigerol variant (CBGV), cannabicyclol (CBL), cannabicyclol (CBN), tetrahydrocannabivarin (THCV), tetrahydrocannabivarinic acid (THCVA), cannabitriol (CBO), cannabinol propyl variant (CBNV), and tetrahydrocannabinolic acid (THCA). Many other useful cannabinoids are disclosed in Agurell et al. (1986) Pharmacol. Rev. 38:31-43. The term cannabinoid also includes prodrugs of cannabinoids, as well as pharmaceutically acceptable salts and complexes of cannabinoids. Ranges useful in the composition according to the disclosure for THC and CBD are about 0.5 mg to about 50 mg, about 1 mg to about 40 mg, about 2 mg to about 30 mg, about 5 mg to about 25 mg, or about 10 mg to about 30 mg.

The cannabinoid is mixed with a solvent into which it solvates or dissolves. As used herein "to solvate" or "solvation" refers to the process of attraction and association of molecules of a solvent with molecules or ions of a solute, here, a cannabinoid. Solvation is the process of surrounding the solute, or cannabinoid, with solvent. It involves evening out a concentration gradient and evenly distributing the solute within the solvent. The solvent may be a pharmaceutically acceptable solvent. Non-limiting examples of useful solvents are e.g., polyethylene glycols (PEG), propylene glycol, substituted polyethylene glycols, propylene carbonate, ethanol, ethyl acetate, isopropyl alcohol, triacetin, triethyl citrate, tributyl citrate, substituted polyethylene glycols, bisabolol, glycerin, mineral oil, ethyl oleate, oleic acid, fatty acid esters, lactic acid, dipropylene glycol, hexylene glycol, propylene carbonate, benzyl benzoate, benzyl alcohol, perillyl alcohol, dibutyl sebacate, phenyethyl alcohol, n-methyl pyrrolidone, dimethyl sulfoxide, 2-pyrrolidone, squalane, animal oils, vegetable oils, dimethyl isosorbide, hydrogenated vegetable oils, isopropyl myristate, limonene, isopropyl palmitate, glycofurol, terpenes, essential oils, alcohols, diols such as ethanol, polyols, silicone fluids, and combination thereof. One exemplary solvent is the alcohol ethanol. Non-limiting ranges of solvent(s) is from about 0.5% to about 95.0%, about 1% to about 80%, about 5% to about 70%, or about 15% to about 35% weight/weight solvent to cannabinoid.

The solvated cannabinoid is then added to an adsorbent. This process creates a film of the solvated cannabinoid (the "adsorbate") on the surface of the adsorbent. This adsorbent may be a pharmaceutically acceptable adsorbent.

One non-limiting adsorbent is silica. The term "silica" encompasses materials that contain silicon dioxide including, but not limited to, amorphous silica, hydrated silicon dioxide, fumed silica, silica gel, colloidal silicon dioxide, magnesium aluminum silicate, magnesium silicate, calcium silicate, and/or mixtures thereof. Useful, non-limiting adsorbents include silica, microcrystalline cellulose, cellulose, silicified microcrystalline cellulose, clay, talc, starch, pregelatinized starch, calcium carbonate, dicalcium phosphate, magnesium carbonate, and mixtures thereof.

Specific useful silicas include, but are not limited to, e.g. ZEOPHARM 5170, AEROSIL 200, CABOSIL MP5, AEROPERL 300, SYLOID 244FP, SYLOID 63FP, SYLOID 72 FP, SIPERNAT 160PQ, SIPERNAT 50, SIPERNAT 50S, SYLOID 3050, SYLOID 3150, SIPERNAT 500LS, SIPERNAT 2200, SIDENT 8, SIDENT 9, SIDENT 10, SIDENT 22S. The useful silica to cannabinoid solvate ratio ranges in the composition according to the disclosure for THC and CBD are about 1.0:0.5 to about 1.0:5.0, about 1.0:2.0 to about 1.0:3.0, or about 1.0:1.0 to about 1.0:1.5.

Excipients can be added to the solvated cannabinoid/adsorbent to aid in the performance or processing of the solid dosage form composition. These can include pharmaceutically acceptable water-soluble diluents, disintegrants, lubricants, glidants, co-solvents, or combinations thereof.

Useful water-soluble diluents may be pharmaceutically acceptable. Useful diluents include, but are not limited to, sugars, polyols, saccharides, polysaccharides, dextrate, dextrins, dextrose, fructose (ADVANTOSE FS 95), lactitol (FINLAC DC), lactose, erythritol, maltose, isomalts, maltitol, a maltodextrin, a polydextrose, trehalose, mannitol (PEARLITOL 300 DC, PEARLITOL 400 DC, PEARLITOL 500 DC, MANNOGEM 2080, MANNOGEM EZ, PARTEKM100, PARTECK M200, PARTECK M300), a polyethylene glycol, sorbitol (PARTECK S1 150, PARTECK S1 400, PARTECK S1 450), sucrose, xylitol and mixtures thereof. One exemplary diluent is mannitol. Non-limiting ranges are from about 5% to about 95%, about 45% to about 90%, or about 55% to about 85% weight/weight per dosage unit.

Another useful non-limiting excipient is a disintegrant which may be pharmaceutically acceptable. Useful disintegrants include, but are not limited to, sodium starch glycolate, crospovidone, croscarmellose sodium, low-substituted hydroxypropyl cellulose, starch, pregelatinized starch, microcrystalline cellulose, and mixtures thereof. One exemplary disintegrant is low-substituted hydroxypropyl cellulose. The useful non-limiting content of the disintegrant in the composition may be from about 0.5% to about 25%, from about 1% to about 20%, from about 2% to about 15%, or from about 3% to about 9% weight/weight per dosage unit.

Yet another useful non-limiting excipient is a lubricant, which may be pharmaceutically acceptable. Useful lubricants include, but are not limited to, sodium stearyl fumarate, magnesium stearate, stearic acid, sodium lauryl sulfate, talc, polyethylene glycol, calcium stearate, /or mixtures thereof. One exemplary lubricant is sodium stearyl fumarate. The non-limiting content of the lubricant in the composition may be from about 0.1% to about 5.0%, from about 0.5% to about 3.0%, or from about 1% to about 2% weight/weight per dosage unit.

The formulation may contain solvents such as, but not limited to ethanol, propylene glycol, polyol, alcohol, polyethylene glycol, substituted polyethylene glycols, propylene carbonate, or a mixture thereof. The useful non-limiting content of the solvent ethanol, for the composition according to the disclosure for THC and CBD are about 0.5% to about 95.0%, from about 1% to about 80%, from about 5% to about 70%, or from about 15% to about 35% weight/weight solvent to THC/CBD.

Other useful excipients that can comprise the composition include, but are not limited to, a colorant, a flavoring, a coating agent, a binder, a diluent, a glidant, a film-forming polymer, an opacifying agent, a humectant, a granulating agent, a gelling agent, a polishing agent, a suspending agent, a sweetening agent, an anti-adherent, a preservative, an antioxidant, a chelating agent, a plasticizer, a tonicity agent, a viscosity agent, a controlled-release agent, a wax, a wetting agent, a thickening agent, a stiffing agent, a stabilizing agent, a sequestering agent, a mucoadhesive, a sialagogic agent, an essential oil, an emollient, a dissolution enhancer, a dispersing agent, a buffering agent (e.g., phosphate, carbonate, tartrate, borate, citrate, acetate, and malate buffers) and combinations thereof.

The method of manufacture for a solid dosage form for sublingual or buccal administration according to the present disclosure may employ any suitable method known in the art including, but not limited to, directly compressing the solvated cannabinoid/adsorbent into a tablet form. Other methods to process the solvated cannabinoid/adsorbent include, but are not limited to, added to premanufactured tablets, cold compressions with inert fillers and binders, direct powder blends, wet or dry granulations, film casting, molding, layer tablets, lyophilization, microencapsulation, freeze drying, spray-congealing, spray-drying, co-melt, spheronization, triturates, troching, powder layering, pelleting, encapsulation, pilling, and combinations thereof.

For example, the solid dosage form may be a tablet containing from about 0.1 mg to about 150 mg, from about 0.5 mg to about 50 mg, from about 1 mg to about 40 mg, from about 2 mg to about 30 mg, from about 5 mg to about 25 mg, or from about 10 mg to about 20 mg of a cannabinoid. The solvent is present in an amount ranging from 0.5% to about 95.0%, from about 1% to about 80%, from about 5% to about 70%, or from about 15% to about 35% weight/weight solvent to cannabinoid. The adsorbent silica can be present in a silica with a silica to cannabinoid solvate ratio ranging from about 1.0:0.5 to about 1.0:5.0, from about 1.0:2.0 to about from 1.0:3.0, or from about 1.0:1.0 to about 1.0:1.5. The level of cannabinoid solvate:silica adsorbent in the solid dosage form ranges from about 0.5% to 40%, from about 1% to about 35%, from about 5% to about 30%, or from about 10% to about 20% weight/weight to the dosage form. A water-soluble diluent, but not limited to, mannitol, can be present in an amount ranging from about 5% to about 95%, about 45% to about 90%, or from about 55% to 85% weight/weight per dosage unit. It is understood by the skilled artisan, that use of the term "about" includes the range as stated, are within what is normally acceptable in the pharmaceutical industry. The US Pharmacopeia allows a plus and minus range of 10% in the assay for the active ingredient in most solid dosage forms.

One non-limiting example of the preparation of a solid tablet form of the composition according to the disclosure is shown in FIG. 1. THC is solvated in ethanol, and then adsorbed to silica to form a THC/silica/adsorbent. Other excipients are then added to the THC/silica/adsorbent, which is then compressed into sublingual/buccal tablets. In one embodiment, the excipients added is mannitol, low-substituted hydroxypropyl cellulose, and/or sodium stearyl fumarate, to form a final blend composition. The final blend is compressed into 85 mg tablets using 0.25 inch round tooling to prepare a 5 mg strength THC sublingual tablet.

The sublingual/buccal tablets may be packaged in such a manner as to aid in maintaining stability. Packaging methods and materials may include, but are not limited to, blister packaging in a foil/foil, foil/Acrylonitrile, foil/polychlorotrifluoroethylene laminates, or placed into glass and plastic bottles.

The composition according to the disclosure can be used or administered by placing it under the tongue, or in the buccal cavity, and leaving it undisturbed until it disintegrates, which typically occurs within 15 minutes, more or less. The amount of cannabinoid to be administered and how often is determined by the condition being treated.

For example, the composition according to the disclosure can be used in the treatment of any disorder for which a cannabinoid has therapeutic properties. Non-limiting examples of such disorders include AIDS, cancer, and malignant tumors, which are often accompanied with a lack of appetite, nausea, and vomiting, chronic pain (especially neuropathic pain), spasticity (e.g., in multiple sclerosis and spinal cord injury), dystonia, intractable pediatric epilepsy. Other disorders treatable with the formulation according to the present disclosure include oxidation-associated disease such as myocardial infarction, stroke (motor or sensory abnormalities and cerebral infarct, or a neurovascular thromboembolic event. The composition may be administered in combination with other therapeutic drugs. The amount and manner of treatment comprising administration of the cannabinoid composition according to the disclosure is determined by a medical professional.

The composition may also be prepared for recreational use or use as a supplement.

The critical sublingual/buccal tablet attributes which reflect the product's in vivo performance characteristics are disintegration and dissolution. Useful, non-limiting methods used to determine disintegration, dissolution, pharmacodynamic and the pharmacokinetic attribute of the sublingual/buccal tablet are described below in the Examples.

While rapid tablet disintegration is prerequisite for rapid drug release from a tablet, drug dissolution from the dosage form actually measures whether the drug is available for absorption through the oral mucosa. A useful method for measuring rapidly disintegrating sublingual tablets in vitro was developed by Rachid et al. (*AAPS Pharm. SciTech* (2011) 12(2):544-52). (See Example 4 below.) An alternative method to evaluate dissolution of sublingual tablets is the USP Dissolution Method <711>. Short drug dissolution times can be evaluated using this method in small volumes, i.e., 2 ml, which is comparable to the amount of salvia in the oral cavity rather than the 900 ml used for oral tablets dissolution in USP <711>.

Reference will now be made to specific examples illustrating the disclosure. It is to be understood that the examples are provided to illustrate exemplary embodiments and that no limitation to the scope of the disclosure is intended thereby.

EXAMPLES

Example 1

Sublingual/Buccal Tablet Formulation

A 5 mg strength THC sublingual/buccal tablet having a total tablet weight of about 85 mg is comprised of a THC, ethanol, silica, mannitol, low-substituted hydroxypropyl cellulose, and sodium stearyl fumarate. An exemplary formulation manufactured for this embodiment and in accordance with the subject invention is provided in Table 1, below. This tablet formulation was used for disintegration, dissolution and pharmacodynamic testing conducted herein.

TABLE 1

| INGREDIENT | AMOUNT (mg/tablet) |
|---|---|
| THC | 5.00 |
| Ethanol | 2.50 |
| Silica | 5.00 |

TABLE 1-continued

| INGREDIENT | AMOUNT (mg/tablet) |
|---|---|
| Mannitol | 58.30 |
| Low-substituted hydroxypropyl cellulose | 12.50 |
| Sodium Stearyl Fumarate | 1.70 |
| Total Tablet Weight | 85.00 |

The tablet is prepared by solvating THC with ethanol to make a solution with or without a co-solvent. The drug solution is then adsorbed to silica. The solvated THC/silica mixture is blended using a tumble blender with mannitol as the water-soluble diluent, low-substituted hydroxypropyl cellulose as a disintegrant, and sodium stearyl fumarate as a lubricant and this blend is directly compressed on a tablet press using 0.2500 inch, round, standard concave tooling into a tablet for sublingual/buccal administration.

Example 2

Cannabidiol Tablet Formulation

A 10 mg strength CNB sublingual/buccal tablet having a total tablet weight of about 144 mg, is prepared. This tablet comprises of ethanol, silica, mannitol, low substituted hydroxypropyl cellulose, and sodium stearyl fumarate, in amounts shown in Table 2.

TABLE 2

| INGREDIENT | AMOUNT (mg/tablet) |
|---|---|
| Cannabidiol | 10.00 |
| Ethanol | 2.60 |
| Silica | 8.40 |
| Mannitol | 98.88 |
| Lo-substituted hydroxypropyl cellulose | 21.12 |
| Sodium Stearyl Fumarate | 3.00 |
| Total Tablet Weight | 144.00 |

The tablet is prepared by solvating CNB into ethanol by mixing at room temperature. The drug solution is then adsorbed to silica. The solvated CBD/silica mixture is then blended using a tumble blender with mannitol as the water-soluble diluent, low-substituted hydroxypropyl cellulose as a disintegrant, and sodium stearyl fumarate as a lubricant in a tumble blender. This blend is directly compressed into a tablet on a tablet press using 0.2812 inch, round, standard concave tooling.

Example 3

Disintegration Testing

The THC composition according to Example 1 was tested for disintegration using the USP Disintegration Method <701>. The standard apparatus and basket assembly without the use of disc was used for measuring the disintegration of sublingual tablets.

The USP monographed acceptance criteria for Sublingual Nitroglycerin Tablet all six tablets have to disintegrated within 2 min. The results for THC sublingual tablets according to Example 1 meets the USP acceptance criteria for Sublingual Nitroglycerin Tablets being less than 2 min with all six tablets disintegrated rapidly between 21 sec and 41 sec.

Example 4

Dissolution Testing

Figure 2:
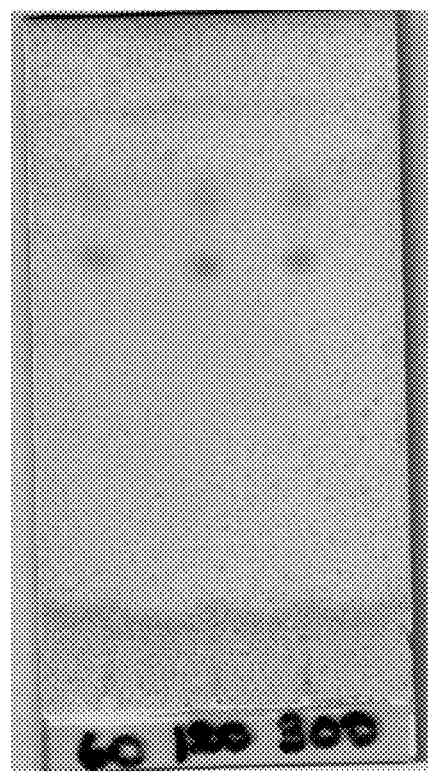
FIG. 2 is a photographic representation of the TLC plate showing the red THC spots obtained from the dissolution of tablet from Example #1 at 60 seconds, 120 seconds, and 300 seconds.

The dissolution of the THC sublingual tablets according to Example 1 were evaluated using the Rachid method at 60 sec, 120 sec, and 300 sec using 2 ml of 0.1 M phosphate buffer, pH 6.8, with 2% Tween 20 as the dissolution media. THC concentrations in the dissolution media were assayed by thin layer chromatography (TLC) (Cannalytics Supply, Denver, Colo.). The dissolution time points were assayed for THC by extracting 1 ml of dissolution media from each time point with 1 ml of the chlorinated hydrocarbon solvent provided in the kit for eluting the TLC plate. A total of 20 µl sample from the chlorinated hydrocarbon extract was deposited on the TLC plate for each time point. The TLC plate was developed and stained to determine the amount of THC at each time point. A photograph of the developed TLC plate is shown in FIG. 2.

The developed TLC plate shows that the size of the red spots at 120 sec and 300 sec are comparable. At the 60 sec time point they appear similar in size or slightly smaller. This demonstrates that the critical tablet attribute of THC dissolution is rapid, occurring within 2 min, and therefore available for absorption through the oral mucosa.

Example 5

Pharmacodynamic and Pharmacokinetic Testing

To determine the pharmacodynamics effects of the 5 mg sublingual THC tablet volunteers, who were familiar with the effects of *cannabis*, placed the THC sublingual tablet, as embodied herein in Example 1, under the tongue and left it undisturbed. Shortly thereafter, i.e., within about 5 minutes, the pharmacological effects of THC were apparent to all volunteers. This included mild euphoria, elation, merriment and heightened sensory awareness. The symptoms peaked in about 30 minutes and continued for several hours thereafter.

Another useful measure of product's in vivo performance would be to measure drug plasma levels in open-label study in volunteers in which blood samples of 5 ml are drawn at times 0 (predose), 4 min, 8 min, 10 min, 12 min, 16 min, 30 min, 45 min, 60 min, 90 min, 120 min and 180 min after administration of the cannabinoid composition according to the disclosure. Harvested plasma is kept at −20° C. until analysis by gas chromatography/tandem mass spectrometry (GC-MSMS) or liquid chromatography tandem mass spectrometry (LC-MSMS). The pharmacokinetic outcomes measured are: time to maximum plasma concentration ($T_{max}$); maximum plasma concentration ($C_{max}$); and the area under the plasma curve (AUC).

EQUIVALENTS

Those skilled in the art will recognize, or be able to ascertain, using no more than routine experimentation, numerous equivalents to the specific composition and procedures described herein. Such equivalents are considered to be within the scope of this disclosure, and are covered by the following claims.

What is claimed is:

1. A pharmaceutical composition, comprising:
    a pharmaceutically-acceptable adsorbent, and adsorbed thereto a cannabinoid solution comprising a mixture of ethanol and a cannabinoid selected from the group consisting of delta-9-tetrahydrocannabinol (THC), cannabidiol (CBD) and mixtures thereof; wherein
    the pharmaceutical composition is a solid dosage form;
    the solid dosage form is a tablet, powder, or film;
    dissolution of the cannabinoid occurs within 300 seconds in 0.1 M phosphate buffer, pH 6.8, with 2% polysorbate 20;
    the pharmaceutically-acceptable adsorbent is silica;
    the cannabinoid is present in an amount from about 0.1 mg to about 150 mg; and
    the weight/weight ratio of silica:cannabinoid solution is from about 1:0:0.5 to about 1.0:5.0; and
    the cannabinoid solution in the solid dosage form comprises from about 5 wt % to about 95 wt % of ethanol by weight of the cannabinoid solution.

2. The pharmaceutical composition of claim 1, wherein the silica is silicon dioxide, amorphous silica, hydrated silicon dioxide, fumed silica, colloidal silicon dioxide, magnesium aluminum silicate, magnesium silicate, calcium silicate, or a mixture thereof.

3. The pharmaceutical composition of claim 1, wherein the cannabinoid is THC.

4. The pharmaceutical composition of claim 3, wherein the THC is present at from about 0.5 mg to about 50 mg.

5. The pharmaceutical composition of claim 3, wherein the THC is present at from about 10 mg to about 30 mg.

6. The pharmaceutical composition of claim 1, wherein the cannabinoid is CBD.

7. The pharmaceutical composition of claim 6, wherein the CBD is present at from about 0.5 mg to about 50 mg.

8. The pharmaceutical composition of claim 6, wherein the CBD is present at from about 10 mg to about 30 mg.

9. The pharmaceutical composition of claim 1, wherein the weight/weight ratio of silica:cannabinoid solution is from about 1.0:2.0 to about 1.0:3.0.

10. The pharmaceutical composition of claim 1, wherein the weight/weight ratio of silica:cannabinoid solution is from about 1.0:1.0 to about 1.0:1.5.

11. The pharmaceutical composition of claim 1, wherein the cannabinoid solution does not comprise an emulsifying agent.

12. The pharmaceutical composition of claim 1, wherein the cannabinoid solution comprises from about 5 wt % to about 70 wt % of ethanol by weight of the cannabinoid solution.

13. The pharmaceutical composition of claim 1, further comprising a water-soluble diluent, a disintegrant, a lubricant, or mixtures thereof.

14. The pharmaceutical composition of claim 13, wherein the water-soluble diluent comprises mannitol.

15. The pharmaceutical composition of claim 13, wherein the disintegrant comprises low-substituted hydroxypropyl cellulose.

16. The pharmaceutical composition of claim 13, wherein the lubricant comprises sodium stearyl fumarate.

17. A composition, comprising:
a solid dosage form of a pharmaceutically acceptable silica, and adsorbed thereto a solvated cannabinoid, the solvated cannabinoid consisting essentially of:
a cannabinoid; and
ethanol;
wherein the solvated cannabinoid in the solid dosage form is from about 5 wt % to about 95 wt % ethanol by weight of the solvated cannabinoid.

18. The composition of claim 17, wherein the solvated cannabinoid is from about 5 wt % to about 70 wt % ethanol by weight of the solvated cannabinoid.

* * * * *